(12) United States Patent
Koren

(10) Patent No.: US 6,315,444 B1
(45) Date of Patent: Nov. 13, 2001

(54) ENVELOPES FOR REUSABLE X-RAY MEDIA

(75) Inventor: Jacob Koren, Haifa (IL)

(73) Assignee: Digident Ltd., Nesher (IL)

( * ) Notice: Subject to any disclaimer, the term of this patent is extended or adjusted under 35 U.S.C. 154(b) by 0 days.

(21) Appl. No.: 09/357,485

(22) Filed: Jul. 20, 1999

(51) Int. Cl.⁷ .................................................... A61B 6/14
(52) U.S. Cl. ............................................ 378/169; 378/168
(58) Field of Search ................................ 378/167, 168, 378/169, 170

(56) References Cited

U.S. PATENT DOCUMENTS

| | | | |
|---|---|---|---|
| 1,698,795 | * 1/1929 | Hillman | 378/168 |
| 4,913,288 | * 4/1990 | Tanaka | 378/169 |
| 4,922,511 | * 5/1990 | Gay | 378/168 |
| 5,466,561 | * 11/1995 | Rantanen | 378/169 |
| 5,864,146 | * 1/1999 | Karellas | 378/191 |

* cited by examiner

*Primary Examiner*—Drew Dunn
(74) *Attorney, Agent, or Firm*—Ladas and Parry

(57) ABSTRACT

A container for an imaging plate includes a sealable envelope, in which the plate is inserted, and one or more flaps, fixed to the envelope, which are closed by an operator so as to seal the plate inside the envelope. The flaps are then pulled open by the operator in order to release the plate from the envelope substantially without physical contact by the operator with the plate. Typically, the flaps are folded over the envelope and fixed one to another, creating a fold that seals the envelope shut.

16 Claims, 3 Drawing Sheets

ENVELOPES FOR REUSABLE X-RAY MEDIA

FIELD OF THE INVENTION

The present invention relates generally to digital radiography devices and specifically to devices for dental radiography based on reusable X-ray media.

BACKGROUND OF THE INVENTION

Historically intraoral dental radiography has been based on X-ray film. Since the film is used only once, there is no need for re-sterilization after use.

Recently, however, the dental field is moving toward digital radiography systems with reusable image receivers, such as Photostimulable Phosphor (PSP) plates. A PSP plate is inserted in the patient's mouth and exposed to X-rays, like a standard film. The exposed plate is removed from the mouth and "developed" by a laser scanner, whereupon the image on the plate is displayed and stored by a computer. The plate is then erased, by a flash of bright light, and is ready for reuse.

With the advent of reusable image receivers, complications have emerged concerning the sterilization and maintenance of the reusable media. PSP plates are degraded by both the chemicals and heat that can be used to sterilize them between uses. Therefore, the plate must be sealed inside a suitable envelope before it is placed in the mouth. A special procedure must be followed to remove the plate from the envelope for development, in order not to compromise the plate's sterility.

SUMMARY OF THE INVENTION

It is an object of some aspects of the present invention to provide apparatus and method to preserve the sterility of reusable intraoral X-ray imaging media during oral procedures.

In preferred embodiments of the present invention, a reusable imaging media plate, such as a PSP plate, is inserted into a foldable plastic envelope having flaps which fold and seal the plate within the envelope. The seal protects the PSP plate and prevents contact with saliva or other body fluids. Preferably, the envelope comprises a release flap which allows extraction of the sterile PSP plate without physical contact with the plate. The plate thus remains uncompromised, and the necessity of sterilization is eliminated.

There is therefore provided, in accordance with a preferred embodiment of the present invention, a container for an imaging plate including:

a sealable envelope, in which the plate is inserted; and one or more flaps, fixed to the envelope, which are closed by an operator so as to seal the plate inside the envelope, and which are pulled open by the operator in order to release the plate from the envelope substantially without physical contact by the operator with the plate.

Preferably, the one or more flaps are folded over the envelope, creating a fold that seals the envelope shut, wherein the one or more flaps are folded and fixed one to another in order to seal the envelope.

Further preferably, at least one of the flaps has a perforation, which is torn so as to pull the flap open. Preferably, the envelope includes first and second sides, which are peeled apart to open the envelope, wherein at least one of the flaps includes first and second sides connected respectively to the first and second sides of the envelope, such that the operator grasps and pulls the first and second sides of the at least one of the flaps to peel apart the envelope.

Typically, the imaging plate includes a reusable X-ray sensitive medium, wherein the imaging plate inside the container is inserted into the mouth of a patient for producing X-ray images thereof.

In a preferred embodiment, the container includes substantially opaque cover, which receives the imaging plate and inside which cover the plate is inserted into the envelope. Preferably, the cover further receives an X-ray shield, parallel to the imaging plate, for intercepting spurious X-rays.

There is also provided, in accordance with a preferred embodiment of the present invention, a method for preserving sterility of an imaging plate, including:

inserting the plate into a sealable envelope;

closing one or more flaps on the envelope so as to seal the plate inside the envelope;

exposing the plate to form an image thereon; and pulling the one or more flaps open in order to release the plate from the envelope, substantially without making physical contact with the plate.

Preferably, closing the one or more flaps includes folding the flaps over the envelope so as to create a fold that seals the envelope shut, wherein folding the flaps includes fixing the flaps one to another in order to seal the envelope. Most preferably, pulling the one or more flaps includes tearing at least one of the flaps along a perforation thereon.

Further preferably, pulling the one or more flaps includes peeling apart first and second sides of the envelope using the flaps, wherein pulling the one or more flaps includes releasing the plate onto a receiving surface without touching the plate.

Preferably, the imaging plate includes a reusable X-ray sensitive medium, wherein exposing the plate includes inserting the plate in the container into the mouth of a patient so as to produce X-ray images thereof.

The present invention will be more fully understood from the following detailed description of the preferred embodiments thereof, taken together with the drawings in which:

DETAILED DESCRIPTION OF PREFERRED EMBODIMENTS

Figure 1:
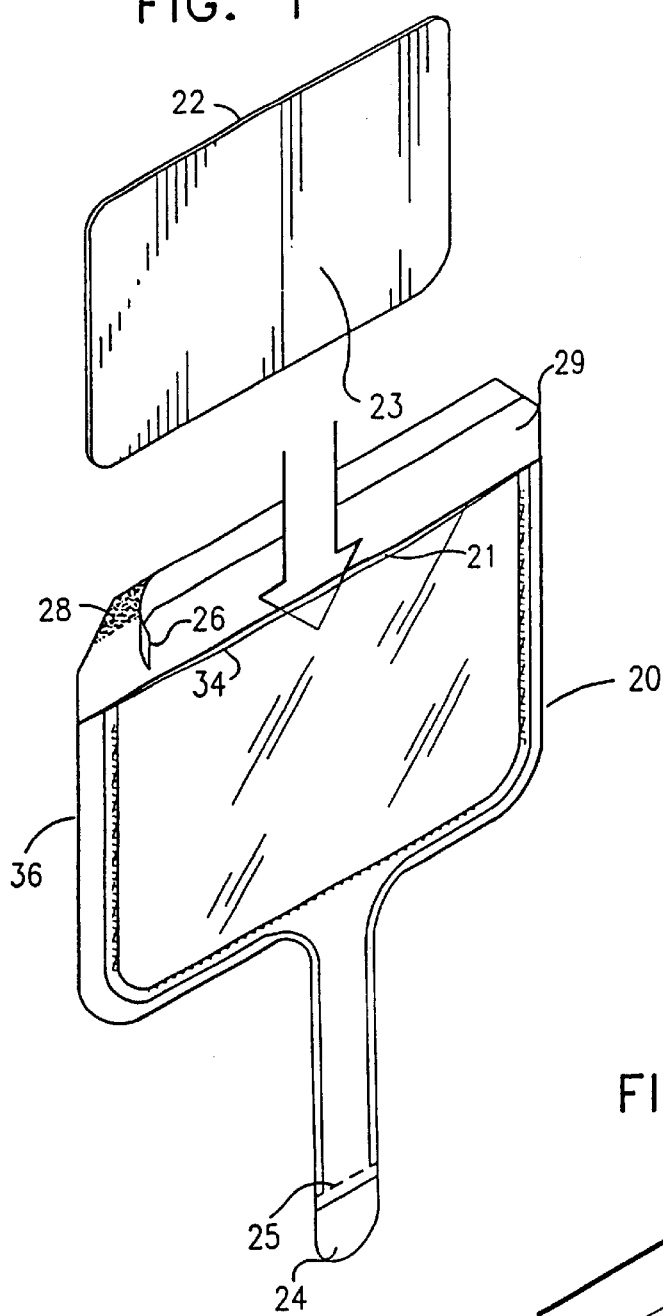
FIG. 1 is a simplified, pictorial illustration showing insertion of a reusable imaging plate into an envelope, in accordance with a preferred embodiment of the present invention.

Reference is now made to FIG. 1, which is a simplified, pictorial illustration showing insertion of a reusable imaging plate 22 into an envelope 20, in accordance with a preferred embodiment of the present invention.

Envelope 20 comprises a receptacle 21 which receives and holds a reusable image receiver plate 22. Preferably plate 22 is a PSP plate, having a radiation-sensitive face 23, and is inserted with face 23 facing forward, i.e. facing a front face 34 of envelope 20 as shown in FIG. 1. Additionally, envelope 20 comprises a closure flap 29, and a release flap 24, whose functions are described hereinbelow.

Figure 2:
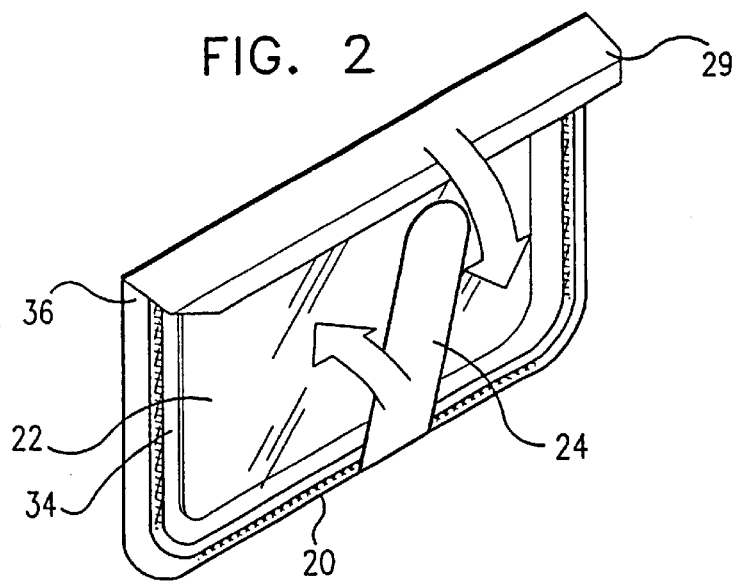
FIG. 2 is a simplified, pictorial illustration showing the envelope of FIG. 1 after insertion of the plate.

Preferably, front face 34 of receptacle 21 is transparent, allowing face 23 of plate 22 to be seen and aiding in proper insertion of the plate in a patient's mouth (FIG. 2). Moreover, preferably a rear face 36 of receptacle 21 is opaque, protecting plate 22 from exposure to light and consequent fading. Faces 34 and 36 are made of a non-toxic, flexible plastic and are heat-sealed around an outer edge thereof, except for the opening through which the plate is inserted.

Preferably, flap 24 is perforated along a line 25. Flap 29 has a peel-off tab 26 covering an adhesive coating 28. The functions of these elements are described hereinbelow.

FIG. 2 is a simplified, pictorial illustration of envelope 20, after insertion of plate 22 into receptacle 21. Flap 24 and flap 29 are folded over to seal the plate inside receptacle 21, such that flap 29 is folded over flap 24 and fixes flap 24 to face 34. Note that the fold in flap 29 bends faces 34 and 36 together such that the opening in receptacle 21 is closed off.

Figure 3:
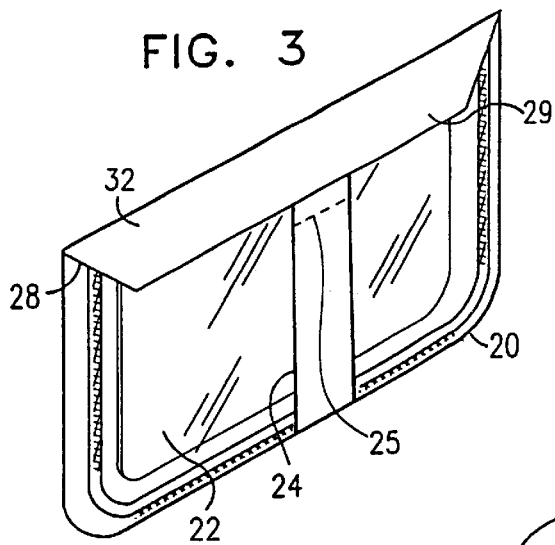
FIG. 3 is a simplified, pictorial illustration showing sealing of the envelope.

FIG. 3 is a simplified, pictorial illustration showing sealing of plate 22 into envelope 20. Flap 29 is fully folded over, creating a fold 32 which folds faces 34 and 36 over onto themselves, and seals shut the opening of receptacle 21. Fold 32 forms a barrier against the entrance of bodily fluids, such as saliva, into receptacle 21. In this configuration, envelope 20 with plate 22 inside is inserted into a patient's mouth.

Figure 4:
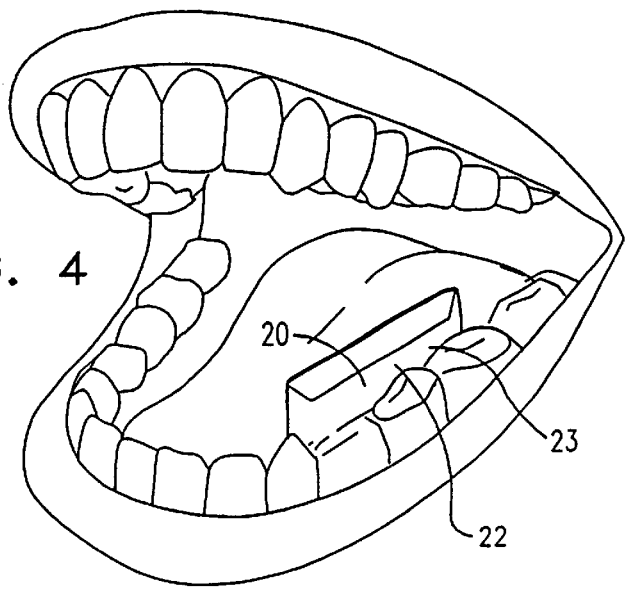
FIG. 4 is a simplified, pictorial illustration showing the envelope containing the plate in use in a patient's mouth, in accordance with a preferred embodiment of the present invention.

FIG. 4 is a simplified, pictorial illustration showing sealed envelope 20 containing plate 22, in use in a patient's mouth, in accordance with a preferred embodiment of the present invention. Envelope 20, with plate 22 sealed within it, is positioned in a patient's mouth behind the teeth designated to be X-rayed. As shown in the figure, envelope 20 is preferably placed with the folded face directed outward, exposing face 23 of plate 22 to the X-ray beam.

Figure 5:
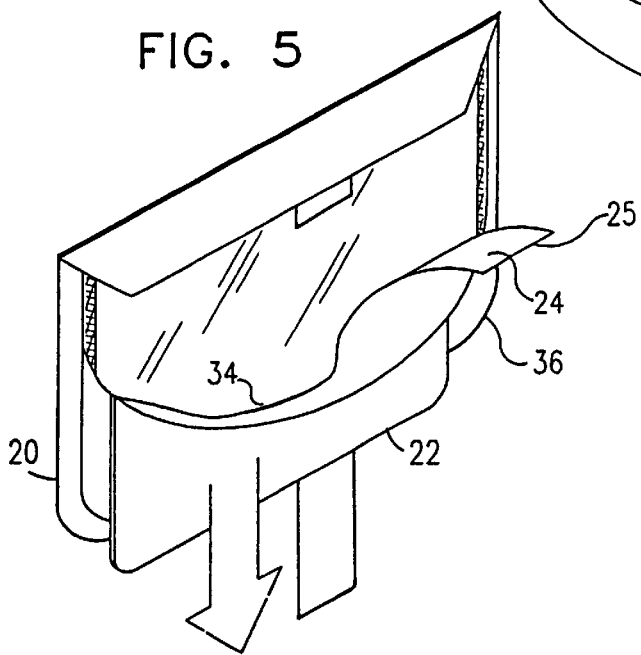
FIG. 5 is a simplified, pictorial illustration showing removal of the plate from the envelope.

FIG. 5 is a simplified, pictorial illustration showing removal of plate 22 from envelope 20 after exposure of an X-ray image. Flap 24 is split along the perforation in line 25, releasing the flap and allowing faces 34 and 36 to be separated. Face 34 is then peeled off from face 36, releasing plate 22 from the seal of receptacle 21. Preferably, plate 22 is then allowed to fall from envelope 20 onto a sterile surface. The dentist preferably performs these steps without removing his gloves, which protect his fingers from contact with saliva on the envelope, while plate 22 is removed from envelope 20 without physical contact with the gloves. Envelope 20 thus preserves the sterility of plate 22 by providing an effective mechanism for protecting the plate from even indirect contact with saliva.

Although in the preferred embodiment described hereinabove, plate 22 is inserted, and envelope 20 is folded and sealed along a length of the envelope, i.e., a horizontal axis as seen in FIG. 1, in alternative embodiments, envelope 20 receives, folds, seals, and releases plate 22 along the width of the envelope, i.e., along a vertical axis in the view of FIG. 1. Additionally, flaps 29 and 24 may have different contours from those shown, as long as they still fulfill the function of effectively sealing plate 22 into envelope 20.

Moreover, although envelope 20 is shown and described herein in intraoral use, the principles of the present invention may be applied to maintain sterility of reusable imaging media in other medical and surgical applications, for example, in intraoperative X-ray imaging.

Figure 6A:
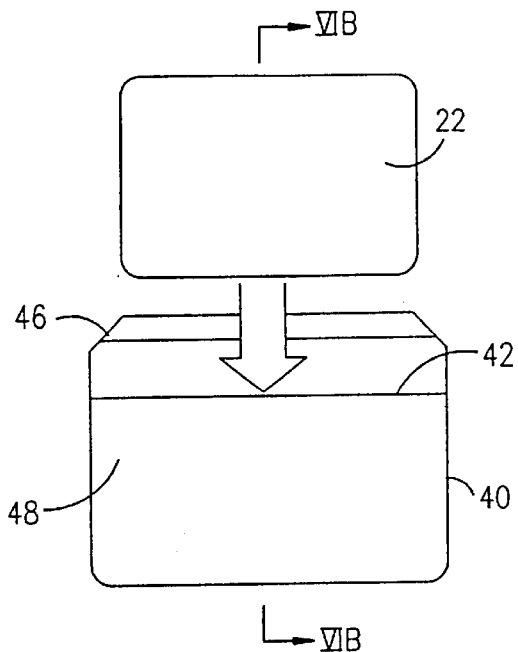
FIG. 6A is a schematic front view of a plate cover, in which a reusable imaging plate is inserted, in accordance with a preferred embodiment of the present invention.
Figure 6B:
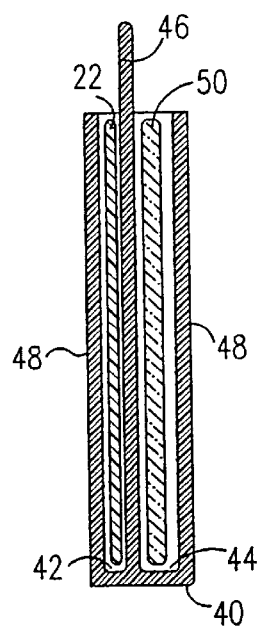
FIG. 6B is a schematic, sectional view of the cover of FIG. 6A, taken along a line VIB—VIB.

FIGS. 6A and 6B are schematic illustrations of a plate cover 40, which receives plate 22 and is then inserted together with the plate into envelope 20, in accordance with a preferred embodiment of the present invention. FIG. 6A is a front view, showing insertion of plate 22 into a pouch 42 formed between an outer layer 48 and a middle layer 46 of cover 40. FIG. 6B is a sectional view of the cover and plate taken along a line VIB—VIB in FIG. 6A.

Cover 40 preferably comprises an opaque, flexible plastic, so that when plate 22 is inserted in the container, the plate is protected from ambient light. Such protection is useful in preventing fading of the latent image formed on the plate by X-ray exposure between the time the plate (in envelope 20) is removed from the patient's mouth and the time the plate is inserted in a "developing" device for processing and digitization of the image. The inventors have found the protection to be particularly important when the dentist takes a sequence of images at different locations in the patient's mouth, and then develops all the images at once. In such a case there may be a substantial delay between exposing the image and developing it, during which time ambient light striking the plate can cause noticeable image degradation. Plate 22 is thus removed from cover 40 only immediately before development. The cover remains sterile, and can be reused without the need for cleaning or other processing.

As shown in FIG. 6B, cover 40 preferably includes a second pouch 44, similar to pouch 42. Pouch 44 is intended to receive an X-ray shield 50, preferably comprising a small sheet of lead, which is of the same general size and shape as plate 22. Cover 40 is inserted into envelope 20 and positioned in the patient's mouth so that plate 22 faces toward the tooth or teeth to be imaged, and shield 50 faces toward the inside of the mouth. The shield is required by some regulatory authorities in order to protect the mouth from radiation passing through the plate. Cover 40 thus provides a simple and convenient means for providing the required protection. It is also useful in preventing image degradation due to "back-scattered" radiation, which can occur when X-rays pass through plate 22, scatter from other tissues in the mouth, and then strike the plate again. By absorbing substantially all such radiation, shield 50 helps to prevent loss of image contrast and addition of noise due to backscattering.

It will be appreciated generally that the preferred embodiments described above are cited by way of example, and the full scope of the invention is limited only by the claims.

What is claimed is:

1. A container for an imaging plate comprising:
 a sealable envelope, in which the plate is inserted; and
 first and second flaps, fixed to the envelope, which are shaped so as to be folded such that the first flap is folded over the second flap, while the first flap is fixed against the envelope by an operator so as to seal the plate inside the envelope, and wherein the flaps are adapted to be pulled open by the operator in order to release the plate from the envelope substantially without physical contact by the operator with the plate.

2. A container according to claim 1, wherein when the first flap is folded over the envelope, it creates a fold in the envelope that seals the envelope shut.

3. A container according to claim 1, wherein the second flap has a perforation, which is adapted to be torn so as to release the second flap, thereby to open the envelope.

4. A container according to claim 1, wherein the envelope comprises first and second sides, which are peeled apart to open the envelope.

5. A container according to claim 4, wherein at least one of the flaps comprises first and second sides connected respectively to the first and second sides of the envelope, such that the operator grasps and pulls the first and second sides of the at least one of the flaps to peel apart the envelope.

6. A container according to claim 1, wherein the imaging plate comprises a reusable X-ray sensitive medium.

7. A container according to claim 6, wherein the imaging plate inside the container is inserted into the mouth of a patient for producing X-ray images thereof.

8. A container for an imaging plate, comprising:
   a substantially opaque cover, which receives the imaging plate;
   a sealable envelope, in which the substantially opaque cover containing the imaging plate is inserted; and
   one or more flaps, fixed to the envelope, which are shaped so as to be closed by an operator in order to seal the plate inside the envelope, and which are adapted to be pulled open by the operator in order to release the plate from the envelope substantially without physical contact by the operator with the plate,
   such that sterility of the cover is maintained while the cover is in the envelope, so that the cover can be reused after removal of the imaging plate therefrom without the need for cleaning or other processing.

9. A container according to claim 8, wherein the cover has a pouch for removably receiving an X-ray shield, parallel to the imaging plate, for intercepting spurious X-rays.

10. A method for preserving sterility of an imaging plate, comprising:
    inserting the plate into a sealable envelope having first and second flaps;
    closing the flaps on the envelope so as to seal the plate inside the envelope by folding the first flap over the second flap, while fixing the first flap against the envelope;
    exposing the plate to form an image thereon; and
    pulling the flaps open in order to release the plate from the envelope, substantially without making physical contact with the plate.

11. A method according to claim 10, wherein closing the flaps comprises folding the first flap over the envelope so as to create a fold in the envelope that seals the envelope shut.

12. A method according to claim 10, wherein pulling the flaps comprises tearing at least one of the flaps along a perforation thereon.

13. A method according to claim 10, wherein pulling the flaps comprises peeling apart first and second sides of the envelope using the flaps.

14. A method according to claim 13, wherein pulling the flaps comprises releasing the plate onto a receiving surface without touching the plate.

15. A method according to claim 10, wherein the imaging plate comprises a reusable X-ray sensitive medium.

16. A method according to claim 15, wherein exposing the plate comprises inserting the plate in the container into the mouth of a patient so as to produce X-ray images thereof.

* * * * *